United States Patent [19]
Ikeda et al.

[11] Patent Number: 5,104,874
[45] Date of Patent: Apr. 14, 1992

[54] BENZOQUINONE ANTIALLERGY AND ANTIINFLAMMATORY AGENTS

[75] Inventors: Takafumi Ikeda, Handa; Hiroaki Wakabayashi, Aichi; Masami Nakane, Nagoya, all of Japan

[73] Assignee: Pfizer Inc., New York, N.Y.

[21] Appl. No.: 627,149

[22] Filed: Dec. 13, 1990

[30] Foreign Application Priority Data

Jan. 22, 1990 [JP] Japan ................................. 2-12341

[51] Int. Cl.[5] .................. A61K 31/495; A61K 31/34; C07D 295/00; C07D 307/02
[52] U.S. Cl. .................................... 514/252; 514/461; 514/471; 514/529; 514/553; 514/579; 514/716; 514/727; 544/360; 549/492; 549/495; 552/293; 552/306; 552/310; 548/217; 548/224
[58] Field of Search ............... 544/360; 514/252, 471, 514/529, 553, 579, 716, 727, 461; 549/492, 495; 552/293, 306, 310

[56] References Cited

FOREIGN PATENT DOCUMENTS 62-223150 1/1987 Japan.

OTHER PUBLICATIONS

K. H. König and G. Letsch; Chem. Ber. 92, 1789 (1959).
S. C. Srivastava and U. Hornemann; Angew. Chem. Int. Ed. Engl. 15, 109 (1976).
Rajeev and S. P. Srivastava; Indian J. Chem. Sect. B, 14B (2), 141 (1976).
H. Musso and D. Döpp; Chem. Ber. 99, 1470 (1966).
Carpino et al., CA 111-57173y (1989).
Barr et al., CA 87-197573 (1977).
Ried et al., CA 76-14022q (1972).
Rajeev, CA 85-93998z (1976).

*Primary Examiner*—Cecilia Shen
*Attorney, Agent, or Firm*—Peter C. Richardson; J. Trevor Lumb; James M. McManus

[57] ABSTRACT

A series of 2-amino-5,6-dimethyl-1,4-benzoquinone derivatives, inhibitors of cyclooxygenase and lipoxygenase and useful as antiallergic and antiinflammatory agents.

12 Claims, No Drawings

BENZOQUINONE ANTIALLERGY AND ANTIINFLAMMATORY AGENTS

BACKGROUND OF THE INVENTION

This invention relates to novel benzoquinone compounds and their use. The new compounds of the present invention are inhibitors of both the cyclooxygenase (CO) and lipoxygenase (LO) enzymes, and are of use in the treatment or alleviation of allergic or inflammatory conditions in mammals including human.

Arachidonic acid is known to be the biological precursor of several groups of endogenous metabolites, prostaglandins including prostacyclins, thromboxanes and leukotrienes. The first step of the arachidonic acid metabolism is the release of esterified arachidonic acid and related unsaturated fatty acids from membrane phospholipids, via the action of phospholipase. Free fatty acids are then metabolized either by cyclooxygenase to produce the prostaglandins and thromboxanes or by lipoxygenase to generate hydroperoxy fatty acids which may be further converted to the leukotrienes. The prostaglandins exhibit diverse physiological effects depending upon their structure. For example, PGE and PGA inhibit gastric secretion as well as lower arterial blood pressure. The thromboxane, especially, thromboxane $A_2$ is a potent vasoconstrictor and platelet aggregatory substance. The leukotrienes are the biological source of the slow reacting substance of anaphylaxis (SRS-A), a chemical mediator in allergic bronchial asthma.

Aspirin and most other non-steroidal antiinflammatory drugs inhibit the cyclooxygenase enzyme. Both antiinflammatory activity and analgesic activity associated with these drugs are rationalized in terms of their inhibition of the action of cyclooxygenase. The lipoxygenase inhibiting activity of one agent, AA861 [2,3,5-trimethyl-6-(12-hydroxy-5,10-cyclodecadiynyl)-1,4-benzoquinone], has been reported [see, Yoshimoto et al., Biochem, et Biophys. 713, 470-473 (1982)]. CGS-5391B [(C. E. Hock et al., Prostaglandins, 28, 557-571 (1984)]has recently become known as a combination cycloxygenase and lipoxygenase inhibitor.

Besides, PCT Patent Application PCT/JP84/00452 (WO 85/01289) and Japanese patent publication No. 107958/1988 describe and claim a number of benzoxazolone and benzothiazolone derivatives useful for the treatment of inflammatory conditions and thrombosis.

SUMMARY OF THE INVENTION

The compounds of the present invention are of the formula

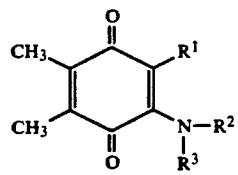
I or the pharmaceutically acceptable salts thereof, wherein; $R^1$ is hydrogen, alkyl of one to five carbon atoms, cycloalkyl of three to seven carbon atoms, phenylalkyl of seven to nine carbon atoms, —COR$^4$ where R$^4$ is alkyl of one to five carbon atoms, phenyl, hydroxy, amino, alkoxy of one to five carbon atoms, omega-carboxyalkyl of two to five carbon atoms or omega-alkoxycarbonylalkyl of three to eight carbon atoms or —CH(OZ)R$^8$ where R$^8$ is hydrogen, alkyl of one to three carbon atoms, omega-carboxyalkyl of two to five carbon atoms or omega-alkoxycarbonylalkyl of three to eight carbon atoms and Z is hydrogen or methoxyethoxymethyl;

$R^2$ is hydrogen or phenyl;

$R^3$ is (a) cycloalkyl of three to seven carbon atoms, (b) cycloalkylalkyl of five to seven carbon atoms which optionally contain an oxygen, sulfur or nitrogen atom as a ring member, (c) a moiety of the formula

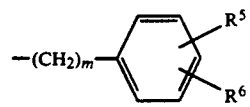

where m is an integer of 0 to 3 and $R^5$ and $R^6$ are each hydrogen, halo, carboxy, carbamoyl, carboalkoxy of two to four carbon atoms, alkoxycarbonylmethyl of three to five carbon atoms, or sulfamoyl, (d) substituted alkyl of the formula R$^7$-alkyl where said alkyl is of five to twelve carbon atoms and R$^7$ is hydroxy, carboxy, carboalkoxy of two to four carbon atoms or hydroxyalkoxy of two to four carbon atoms or furyl and R$^2$ and R$^3$ when taken together with the nitrogen atom to which they are attached form a structure of the formula

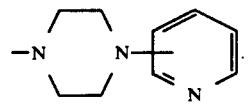

A preferred group of compounds are those where R$^1$ and R$^2$ are each hydrogen. Especially preferred within this group is the compound where R$^3$ is a moiety of the formula

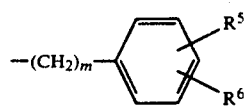

where m is 0 and R$^5$ and R$^6$ are each hydrogen or where R$^3$ is 2-furfuryl.

A second group of preferred compounds are those where R$^1$ is —COR$^4$ or —CH(OZ)R$^8$ where R$^4$ is alkyl of one to five carbon atoms, R$^8$ is alkyl of one to three carbon atoms or hydrogen, Z is hydrogen and R$^2$ is hydrogen. Especially preferred within this group is the compound where R$^1$ is —COR$^4$ where R$^4$ is methyl and R$^3$ is a moiety of the formula

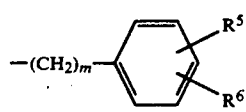

wherein m is 0 and R$^5$ and R$^6$ are each hydrogen and where R$^1$ is —CH(OZ)R$^8$ where R$^8$ is hydrogen or methyl and R$^3$ is a moiety of the formula

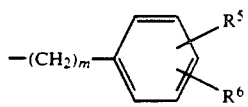

where m is 0 and $R^5$ and $R^6$ are each hydrogen.

A third group of preferred compounds are those where $R^2$ and $R^3$ when taken together with the nitrogen atom to which they are attached form a structure of the formula

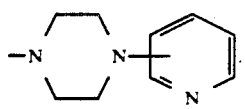

Especially preferred within this group is the compound where $R^1$ is hydrogen and $R^2$ and $R^3$ when taken together with the nitrogen atom to which they are attached form a structure of the formula

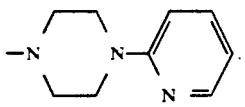

The present invention includes a method for treating an allergic or inflammatory in a human being in need of such treatment which comprises administering to said human being an antiallergic or antiinflammatory effective amount of a compound of formula I.

The present invention also includes a pharmaceutical composition for administration to a human being which comprises a compound of formula I and a pharmaceutically acceptable carrier or diluent.

The term "halo" is meant to include fluoro, chloro, bromo and iodo.

The pharmaceutically acceptable salts of the compounds of the formula (I) are those formed from acids which form non-toxic acid addition salts, for example, the hydrochloride, hydrobromide, sulfate or bisulfate, phosphate, acetate, citrate, fumarate, gluconate, lactate, maleate, succinate, tartrate, methanesulfonate, benzenesulfonate, toluenesulfonate and formate salts. When $R^1$ or $R^3$ contain a carboxy group it is possible to form salts with organic and inorganic bases. These include such organic bases as triethylamine, ethanolamine and triethanolamine, and such inorganic bases as alkali metal hydroxides or alkaline earth metal hydroxides. It is preferred that all these salts be pharmaceutically acceptable.

DETAILED DESCRIPTION OF THE INVENTION

The compounds of formula (I) may be prepared by a number of different routes. In one embodiment, they are prepared from 2-substituted or 2-unsubstituted 5,6-dimethylbenzoquinone (II) and a substituted amine according to the following reaction:

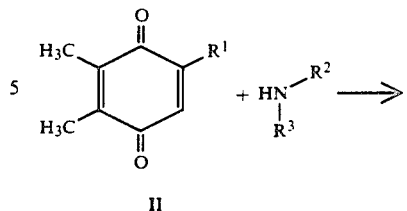

II

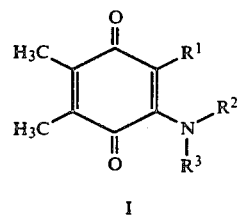

I

In the above formulae, $R^1$, $R^2$ and $R^3$ are as previously defined. The amine substituents, $R^2$ and $R^3$ are preferably H, alkyl, or aralkyl group. The reaction is preferably conducted at ambient temperature in the presence of an oxidizing agent. The oxidizing agent can be benzoquinone (II) itself. Elevated tempertaures can be employed without any significant disadvantage. Suitable solvents which do not react with the reactants and/or products are, for example methanol, ethanol, dichloromethane and chloroform. When a preferred temperature is used, the reaction is substantially complete within a few hours. On completion, product (I) can be isolated and/or purified conventionally, e.g. recrystallization or chromatography.

In another embodiment, the compounds of formula (I) are prepared by the following reaction, using 2-substituted or unsubstituted 5,6-dimethylhydroquinone (III) and a substituted amine:

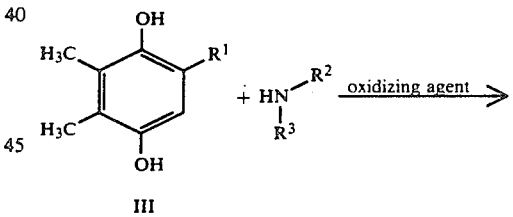

III

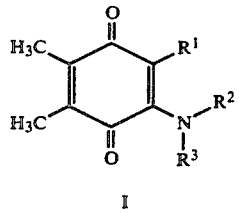

I $(R^3 = H)$

In the above formulae, $R^1$ and $R^2$ are as previously defined. The amine substituent, $R^2$, is preferably an aryl group. The reaction is preferably conducted at ambient temperature in the presence of an oxidizing agent. The oxidizing agent is preferably sodium iodate, although sodium periodate, sodium chlorate or manganese dioxide, can also be employed. Suitable solvents which do not react with the reactants and/or products are, for example, aqueous methanol. When the preferred temperature is used, the reaction usually requires several hours to several days. The product of formula (I) is isolated by standard methods and is purified by conventional means, such as recrystallization or chromatography.

In another emobidment, the compounds of formula (I) ($R^3$ is alkyl, arylalkyl or $R^7$ alkyl) are also prepared from the compounds of formula (I) ($R^3$ is hydrogen) by the following process:

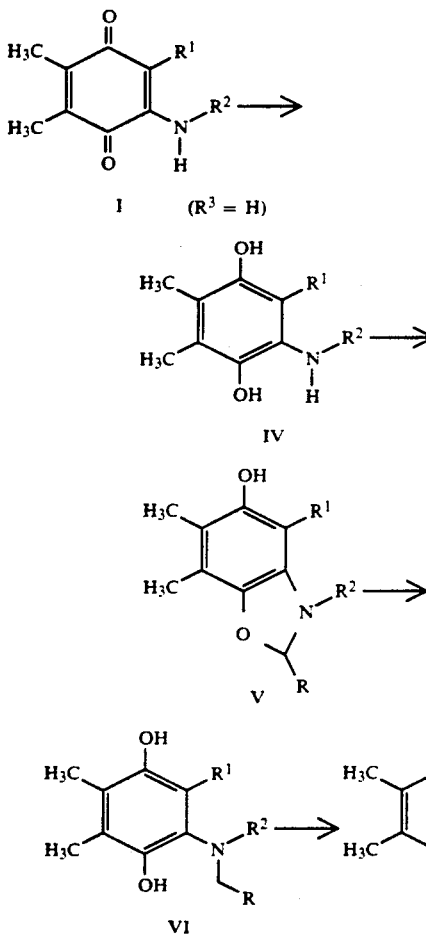

The amine substituents, $R^2$ is preferably aryl and $RCH_2$ is aralkyl or $R^7$ alkyl. In the above formula, $R^1$, $R^2$ and $R^7$ are as previously defined. The first step involves treatment of a group of compounds (I) ($R^3$=H) with a reducing agent. The preferred reducing agent is sodium hydrosulfite, although catalytic hydrogenation such as in the presence of palladium on carbon, can also be employed. The reaction is preferably conducted at ambient temperature. Suitable solvents which do not react with the reactants and/or products are, for example, diethyl ether/water or ethyl acetate/water. When the preferred temperature is used, the reaction usually requires several hours. On completion, product (IV) can be isolated and/or purified conventionally, e.g. recrystallization. It is more convenient not to isolate this product but to subject it to reaction conditions of the second step.

The second step involves a dehydrating reaction with an aldehyde in the presence of an acid. The acid can be either protic or non-protic, such as p-toluenesulfonic acid, camphorsulfonic acid or borontrifluoride etherate. The preferred temperature for this reaction is from 0° to 110° C. Purification of product (V) can be achieved by conventional means such as recrystallization or chromatography. The third step involves reduction of the C—N bond by reaction with an appropriate hydrogen source. For example, compound (V) may be reduced using metal hydrides. The hydride agent suitably employed in this reduction includes sodium borohydride, sodium cyanoborohydride, or lithium cyanoborohydride. This reaction is conducted at ambient temperature, with an excess of a hydride agent in e.g. acetic acid. A preferred temperature for this reaction is from 15° to 50° C. Reduction is ordinarily complete within an hour. On completion, product (VI) can be isolated and/or purified conventionally, e.g. recrystallization. It is more convenient not to isolate this product, but to subject it to a reaction condition of the forth step. The forth step involves oxidation of the hydroquinone (VI) moiety with an appropriate oxidizing agent. For example, compound (VI) may be oxidized with ferric chloride, manganese dioxide, sodium periodate or sodium iodate. The reaction is preferably conducted at ambient temperature. Suitable solvents which do not react with the reactants and/or products are, for example, water and/or methanol. The product of formula (I) is isolated by standard methods and is purified by conventional means, such as recrystallization or chromatography.

The starting materials (II) ($R^1$=H) or (III) ($R^1$=COCH$_3$) are either known compounds or may be prepared by the methods reported in the art reference, see e.g., Etsuro Kurosawa, Bull. Chem. Soc. of Japan, 34, 300 (1961). The other starting materials may be prepared by the following process.

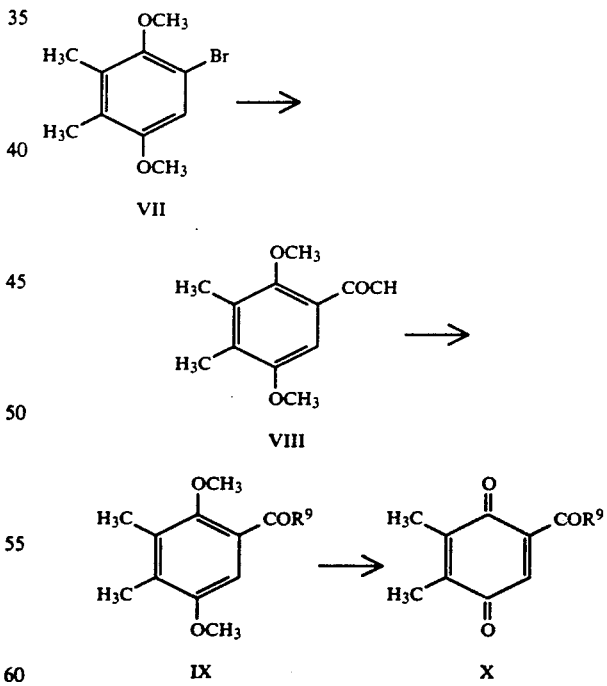

In the above formulae, COR$^9$ may correspond to $R^1$ as previously defined or may be a functional group which can be converted to $R^1$. The first step involves treatment of a group of compounds (VII) with a metalating agent followed by carbon dioxide treatment. The preferred metalating agents are alkyl lithium or magnesium. Suitable solvents which do not react with the reactants and/or products are, for example, diethyl ether, tetrahydrofurane and lower hydrocarbons. On completion, product (VIII) can be isolated and/or purified conventionally, e.g. recrystallization. The second step involves esterification of amidation. These reaction conditions may be conducted by standard procedures, for example, in references, "Comprehensive Organic Chemistry" Sir Deric Barton, F.R.S. and W. David Ollis, F.R.S. Eds., Pergamon press, 1979, vol. 2, pp. 869 and 957.

The third step involves treatment of a group of compounds (IX) with an oxidizing agent. The preferred oxidizing agent is, for example, ceric ammonium nitrate. The oxidation is ordinarily complete within several seconds at ambient temperature. The product of formula (X) is isolated by standard methods and is purified by conventional means, such as recrystallization or chromatography.

Starting material may also be prepared by the following reaction sequence.

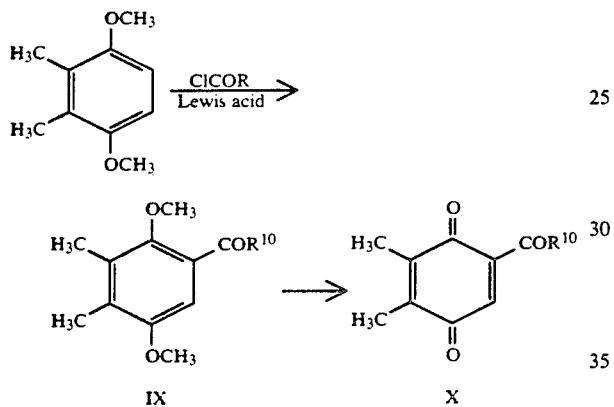

In the above formulae, $COR^{10}$ may correspond to $R^1$ as previously defined or may be a functional group which can be converted to $R^1$. In this particular reaction, acceptable Lewis acid catalysts or solvents may be as described in an art literature, such as "Organic Chemistry," Jerry March, Ed., John Wiley & Sons, Inc., 1985, pp. 484. The acylated product (IX) may be treated with an oxidizing agent. The preferred oxidizing agent is, for example, ceric ammonium nitrate. The oxidation is ordinarily complete within several seconds at ambient temperature. The product of formula (X) is isolated by standard methods and is purified by conventional means, such as recrystallization or chromatography.

The pharmaceutically acceptable salts of the novel compounds of formula (I) are readily prepared by contacting said compound with a stoichiometric amount of an appropriate mineral or organic acid or base in either an aqueous solution or a suitable organic solvent. The salt may then be obtained by precipitation or by evaporation of the solvent. Among those salts enumerated earlier, an especially preferred salt is the hydrochloride or sodium.

The compounds of formula (I) possess inhibiting activity on the action of the cyclooxygenase as well as on the action of the lipoxygenase. This activity has been demonstrated by a cell culture assay using rat peritoneal cavity resident cells which determines the effect of said compounds on the metabolism of arachidonic acid.

The ability of the compounds of formula (I) to inhibit both enzymes make them useful for controlling the symptoms induced by the endogenous metabolites arising from arachidonic acid in a mammalian subject. The compounds are therefore valuable in the prevention and treatment of such disease states in which the accumulation of said arachidonic acid metabolite is the causative factor, e.g., allergic bronchial asthma, skin disorders, rheumatoid arthritis, osteoarthritis, and thrombosis.

Since conventional non-steroidal inflammatory agents such as aspirin only inhibit cyclooxygenase, they suppress inflammatory conditions as well as tend to cause adverse gastrointestinal reaction by virtue of the enzyme inhibition. Compounds of the present invention, however, as gastrointestinally cytoprotective in addition to possessing anti-allergy and antiinflammatory activities. Thus, they show less adverse effects and are of value for use as a safe drug.

When a compound of the formula (I) or a pharmaceutically acceptable salt thereof is to be used as either an anti-allergic agent or an antiinflammatory agent, it can be administered to a human subject either alone, or preferably, in combination with pharmaceutically acceptable carriers or diluents in a pharmaceutical composition, in accordance with standard pharmaceutical practice. A compound can be administered by a variety of conventional routes of administration including orally, parentally and by inhalation. When the compounds are administered orally, the dose range will be from about 0.1 to 20 mg/kg body weight of the subject to be treated per day in single or divided doses. If parental administration is desired, then an effective dose will be from 0.1 to 1.0 mg/kg body weight of the subject to be treated per day. In some instance it may be necessary to use dosages outside these limits, since the dosage will necessarily vary according to the age, weight and response of the individual patient as well as the severity of the patient's symptoms and the potency of the particular compound being administered.

For oral administration, the compounds of formula (I) can be administered, for example, in the form of tablets, powders, lozenges, syrups or capsules, or as an aqueous solution or suspension. In the case of tablets for oral use, carriers which are commonly used include lactose and corn starch, and lubricating agents, such as magnesium stearate, are commonly added. In the case of capsules, useful diluents are lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered.

The present invention is illustrated by the following examples. However, it should be understood that the examples are simply illustrative and the invention is not limited to the specific details of these examples. Proton nuclear magnetic resonance spectra (NMR) were measured at 270 MHz unless otherwise indicated for solutions in chloroform-d1 (CDCl$_3$) and peak positions are expressed in parts per million (ppm) downfield from tetramethylsilance. The peak shapes are denoted as follows: s, singlet; d, doublet; t, triplet; q, quartet; m, multiplet; b, broad.

EXAMPLE 1

2-Anilino-5,6-dimethyl-1,4-benzoquinone

To a stirred solution of 2,3-dimethylhydroquinone (13.8 g, 0.1 mol) and aniline (18.6 g, 0.2 mol) in methanol (600 ml) was added sodium iodate (59.4 g, 0.3 mol) in water (600 ml) at room temperature. The mixture was stirred for 17 hours. The mixture was concentrated (removal of 600 ml of the solvent) and extracted with chloroform (700 ml×3). The combined organic layers were dried and concentrated to a dark red purple oil. This oil was allowed to stand overnight. The residue was solidified and suspended in hexane. The resulting wet precipitates were collected by suction filtration, and the precipitates were suspended in diisopropyl ether. The precipitate was collected by suction filtration. The solid was washed with diisopropyl ether to afford dark brown solid (11.7 g). This (1.05 g) was dissolved in methanol (40 ml) and activated carbon (290 mg) was added. The mixture was stirred at 50° C. for 10 minutes and filtered through celite. The residue was washed with methanol (10 ml). The combined filtrate was concentrated in vacuo. Recrystallization from methanol to afford russet flake crystals of the title compound (500 mg, 47.6%). This was dried at 50° C. for three hours to give the product, mp 115.0°–115.7° C./dec. The second crop was also available from the mother liquid (350 mg, 33%).

$^1$H NMR (270 MHz, CDCl$_3$) delta 7.42–7.33 (3H, m; ph-H×2+NH), 7.22–7.12 (3H, m, ph-H), 6.15 (1H, s, H-3), 2.06–2.03 (6H, m, CH$_3$×2) IR (KBr) ν 3300, 1670, 1645.

Similarly the following compounds were prepared.

| Example No. | R$^1$ | R$^2$ | R$^3$ | m.p. | IR(KBr, cm$^{-1}$) | $^1$H NMR(270MHz, CDCl$_3$, δ) |
|---|---|---|---|---|---|---|
| 2 | H | H | (3,4-dichlorophenyl) | 199–200° C. | 1670, 1640, 1620 1600, 1590 | 7.44(d, 1H, J=9Hz), 7.32(d, 1H, J=3Hz) 7.05(dd, 1H, J=3, 9Hz), 6.13(s, 1H) 2.07(m, 6H) |
| 3$^a$ | H | H | (2-CO$_2$H phenyl) | 210–215° C. | 1690, 1670, 1640 1620, 1600, 1580 | 13.6(br s, 1H), 10.6(s, 1H) 8.02(dd, 1H, J=1, 8Hz), 7.57–7.68(m, 2H) 7.17(ddd, 1H, 1, 6, 8Hz), 6.32(s, 1H) 1.99(br s, 6H) |
| 4$^a$ | H | H | (2-CO$_2$Na phenyl) | >300° C. | 3500(br), 1670 1650, 1610, 1590 | 13.5(s, 1H), 7.97(br d, 1H, J=7Hz) 7.29–7.38(m, 2H) 6.95(ddd, 1H, J=2, 5, 8Hz) 6.24(s, 1H), 1.97(br s, 6H) |
| 5 | H | H | (2-CO$_2$Me phenyl) | 167–170° C. | 1700, 1680, 1610 1600, 1580 | 8.08(br s, 1H), 7.50–7.58(m, 2H) 7.10(ddd, 1H, J=3, 5, 8Hz), 6.43(s, 1H) 3.96(s, 3H), 2.07(br s, 6H) |
| 6 | H | H | (2-CONH$_2$ phenyl) | 200° C. (dec) | 3400, 3200, 1660 1650, 1610, 1580 | 10.43(br s, 1H), 7.46–7.61(m, 3H) 7.11(ddd, 1H, J=2, 6, 8Hz), 6.34(s, 1H) 5.90(br s, 2H), 2.06(s, 6H) |
| 7$^a$ | H | H | (4-CONH$_2$ phenyl) | 211–215° C. (dec) | 3440, 3320, 3200 1660, 1640, 1600 | 9.01(br s, 1H), 7.90(br s, 1H) 7.88(d, 2H, J=9Hz), 7.40(d, 2H, J=9Hz) 7.25(br s, 1H), 6.05(s, 1H) 1.99(br s, 3H), 1.97(br s, 3H) |
| 8 | H | H | (4-CH$_2$CO$_2$Me phenyl) | 101.1–101.6° C. | 1660, 1642, 1610. | 7.30(d, 2H, J=8.4Hz), 7.16(d, 2H, J=8.4Hz 6.13(s, 1H), 3.71(s, 3H) 3.69(s, 2H), 2.06(br s, 6H) |

-continued

| Example No. | R¹ | R² | R³ | m.p. | IR(KBr, cm⁻¹) | ¹H NMR(270MHz, CDCl₃, δ) |
|---|---|---|---|---|---|---|
| 9 | COCH₃ | H | –C₆H₅ | 115.4–116.3° C. | 1675, 1625, 1605 | 12.97(br s, 1H), 7.22–7.41(m, 3H) 7.06(d, 2H, J=6.8Hz), 2.63(s, 3H) 2.10(br s, 3H), 1.96(br s, 3H) |
| 10 | COPh | H | –C₆H₅ | 143.3–143.5° C. | 3340, 1665, 1642 | 7.69(br s, 1H), 7.39–7.52(t, 2H, J=7.7Hz) 6.92–7.00(m, 3H), 6.80–6.82(m, 2H) 2.13(br s, 3H), 2.09(br s, 3H) |

$^a$ ¹H NMR spectrum of this sample was measured in DMSO-$d_6$

EXAMPLE 11

Benzylamino-5,6-dimethyl-1,4-benzoquinone

To a solution of 2,3-dimethyl-1,4-benzoquione (2.72 g, 20 mmol) in methanol (50 ml) was added benzylamine (2.14 g, 12 mmol) at room temperature. After being stirred for 1 hour, the solvent was removed and the residue was purified by a silica gel column chromatography (250 g, eluted with hexane/ethyl acetate). Recrystallization from ethyl acetate and diisopropyl ether gave maroon needle of the title compound (0.82 g, 34%) mp 110°–111° C.

¹H NMR (270 MHz, CDCl₃) delta 7.36–7.26 (5H, m; Ph-H×5), 5.93 (1H, br s; NH), 5.48 (1H, s; H-3), 4.28 (2H, d, J=5.9 Hz, CH₂) 2.03 (3H, br s, CH₃), 2.00 (3H, br s, CH₃).

IR (KBr) v 3300, 1670, 1650

Similarly, the following compounds were prepared.

| Example No. | $R^1$ | $R^2$ | $R^3$ | m.p. | IR(KBr, cm$^{-1}$) | $^1$H NMR(270MHz, CDCl$_3$, δ) |
|---|---|---|---|---|---|---|
| 12 | H | H |  | 147–148° C. | 3380, 1660, 1640 1600 | 7.38(dd, 1H, J=1, 2Hz) 6.34(dd, 1H, J=2, 3Hz) 6.28(dd, 1H, J=1, 3Hz), 5.86(br s, 1H) 5.55(s, 1H), 4.26(d, 2H, J=6Hz) 2.03(br s, 3H), 1.99(br s, 3H) |
| 13 | H | H |  | 112–113° C. | 3380, 2950, 2860 1660, 1640, 1600 | 5.54(br s, 1H), 5.44(s, 1H) 3.15(m, 1H), 2.04(br d, 3H, J=1Hz) 1.98(br d, 3H, J=1Hz), 1.98–2.04(m, 2H) 1.50–1.74(m, 3H), 1.21–1.38(m, 5H) |
| 14 | H | H | 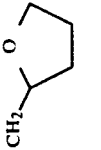 | 92–94° C. | 1670, 1640, 1600 1520 | 5.89(br s, 1H), 5.45(s, 1H) 4.10(ddd, 1H, J=4, 7, 14Hz) 3.74–3.94(m, 2H) 3.22(ddd, 1H, J=4, 6, 14Hz) 3.07(ddd, 1H, J=6, 7, 14Hz) 2.04(br s, 3H), 1.98(br s, 3H) 1.88–2.10(m, 2H), 1.50–1.64(m, 2H) |
| 15 | H | H | (CH$_2$)$_6$—OH | 68–71° C. | 3400, 2950, 2870 1660, 1640, 1600 | 5.61(br s, 1H), 5.42(s, 1H) 3.65(t, 2H, J=6Hz), 3.08(q, 2H, J=6Hz) 2.04(br s, 3H), 1.98(br s, 3H) 1.38–1.72(m, 8H) |
| 16 | H | H | 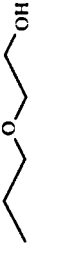 | 82.0–83.5° C. | 3380, 2930, 2870 1660, 1640, 1600 | 5.91(br s, 1H), 5.45(s, 1H) 3.68–3.80(m, 4H), 3.58–3.62(m, 2H) 3.28(q, 2H, J=6Hz), 2.04(br s, 3H) 1.99(br s, 3H), 1.87(t, 1H, J=6Hz) |
| 17 | H | H | (CH$_2$)$_5$—CO$_2$H | 98–99° C. | 3400, 3280, 1740 1680, 1640, 1600 | 5.60(br s, 1H), 5.43(s, 1H) 3.10(q, 2H, J=7Hz), 2.38(t, 2H, J=7Hz) 2.04(br s, 3H), 1.98(br s, 3H) 1.61–1.74(m, 4H), 1.40–1.49(m, 2H) |
| 18 | H | H | (CH$_2$)$_5$—CO$_2$Me | 70–72° C. | 3250, 2950, 1740 1660, 1640, 1600 | 5.56(br s, 1H), 5.42(s, 1H), 3.68(s, 3H) 3.08(q, 2H, J=7Hz), 2.33(t, 2H, J=7Hz) 2.04(br s, 3H), 1.98(br s, 3H) 1.56–1.72(m, 4H), 1.36–1.50(m, 2H) |
| 19 | Me | H | 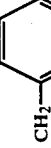 | 103–104° C. | 3380, 1640, 1580 1510 | 7.24–7.39(m, 5H), 5.73(br s, 1H) 4.63(d, 2H, J=6Hz), 2.05(s, 3H) 2.03(br s, 3H), 1.98(br s, 3H) |
| 20 | H | CH$_2$–N–CH$_2$ | 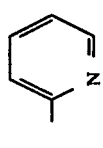 | 108.0–109.9° C. | 3350, 1742, 1650 1610 | 8.42(br d, 1H, J=4Hz) 7.52(ddd, 1H, J=9,1, 7,3, 2.2Hz) 6.62–6.69(m, 2H), 5.76(s, 1H) 3.68–3.73(m, 2H), 3.57–3.52(m, 2H) 2.01(s, 6H). |

-continued

| Example No. | R¹ | R² | R³ | m.p. | IR(KBr, cm⁻¹) | ¹H NMR(270MHz, CDCl₃, δ) |
|---|---|---|---|---|---|---|
| 21 | CO₂Me | H | (phenyl) | 134-136° C. | 3270, 1720, 1590 1510 | 7.88(br s, 1H), 7.09-7.40(m, 5H) 3.21(s, 3H), 2.10(br d, 3H) 2.07(br d, 3H) |
| 22 | CO₂NH₂ | H | (phenyl) | 188-200° C. | 3300(br), 1670 1570(br) | 13.40(br s, 1H), 9.42(br s, 1H) 7.21-7.09(m, 5H), 5.54(br s, 1H) 2.08(br s, 3H), 1.94(br s, 3H) |
| 23 | $\underset{\text{O}}{\overset{\parallel}{\text{C}}}$(CH₂)₃CO₂Me | H | (phenyl) | 104-104.5° C. | 1750, 1660, 1600 1590 | 7.03-7.40(m, 6H), 3.67(s, 3H) 3.07(t, 2H, J = 7Hz), 2.38(t, 2H, J = 7Hz) 2.08(br s, 3H), 1.96(br s, 3H) 1.95(quin, 2H, J = 7Hz) |
| 24 | $\underset{\text{O}}{\overset{\parallel}{\text{C}}}$(CH₂)₃CO₂H | H | (phenyl) | 157-159° C. | 1720, 1670, 1600 1580, 1300 | 12.56(br s, 1H), 7.24-7.40(m, 3H) 7.03-7.08(m, 2H), 3.10(t, 2H, J = 7Hz) 2.43(t, 2H, J = 7Hz), 2.08(br s, 3H) 1.96(br s, 3H), 1.93(quin, 2H, J = 7Hz) |
| 25 | CH₂OH | H | Me | 131-133° C. (dec) | 3460, 3360, 1590 1530 | 4.63(d, 2H, J = 7Hz), 3.25(d, 3H, J = 6H 2.28(t, 1H, J = 7Hz), 2.05(br d, 3H) 1.99(br s, 3H) |
| 26 | | | | | | |

-continued

| Example No. | R¹ | R² | R³ | m.p. | IR(KBr, cm⁻¹) | ¹H NMR(270MHz, CDCl₃, δ) |
|---|---|---|---|---|---|---|

[Structure: 2,3-dimethyl-5-(N-benzyl-N-phenylamino)hydroquinone (4) → NaIO₄ → 2,3-dimethyl-5-(N-benzyl-N-phenylamino)-1,4-benzoquinone (5)]

A stirred solution of 2-anilino-5,6-dimethylbenzoquinone (1) (2.24 g, 0.01 mol) in diethyl ether (100 mL) was added a solution of sodium hydrosulfite (6.96 g, 0.04 mol) in water (20 mL). The mixture was vigorously stirred for 2.5 hours under nitrogen atmosphere. The organic layer was washed with brine and dried over lization from hexane/diisopropyl ether to give russet color powder (100 mg, 12% yield). Mp 119.4°–119.8° C.

$^1$H NMR (270 MHz, CDCl$_3$) delta 7.37–7.15 (8H, m), 7.08 (2H, br. d, J=7.6 Hz), 5.83 (1H, s), 4.94 (2H, s), 1.98 (3H, br. s), 1.92 (3H, br. s). IR (KBr) v 1672, 1649, 1629.

| Example No. | R$^1$ | R$^2$ | R$^3$ | m.p. | IR(KBr, cm$^{-1}$) | $^1$H NMR(270MHz, CDCl$_3$, δ) |
|---|---|---|---|---|---|---|
| 27 | H | 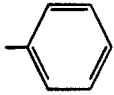 | (CH$_2$)$_5$—CO$_2$H | 95.8–96.2° C. | 3450, 1730, 1678 1650 | 7.58(t, 2H, J=7.9Hz), 7.23(t, 1H, J=7.9Hz) 7.03(d, 2H, J=7.9Hz), 5.74(s, 1H, H-3) 3.65(t, 2H, J=7.5Hz), 2.33(t, 2H, J=7.3Hz) 2.00(br s, 3H), 1.91(br s, 3H) 1.55–1.72(m, 4H), 1.29–1.43(m, 2H) |
| 28$^b$ | H | 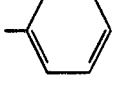 | (CH$_2$)$_5$—CO$_2$Me | oil | 1742, 1670, 1647 1618 | 7.36(t, 2H, J=7.8Hz), 7.23(t, 1H, J=7.8Hz) 7.05(d, 2H, J=7.8Hz) 3.65(s, 3H) 3.65(t, 2H, J=7.8Hz) 2.28(t, 2H, J=7.6Hz), 2.00(br s, 3H) |
| 29 | | | | | | |

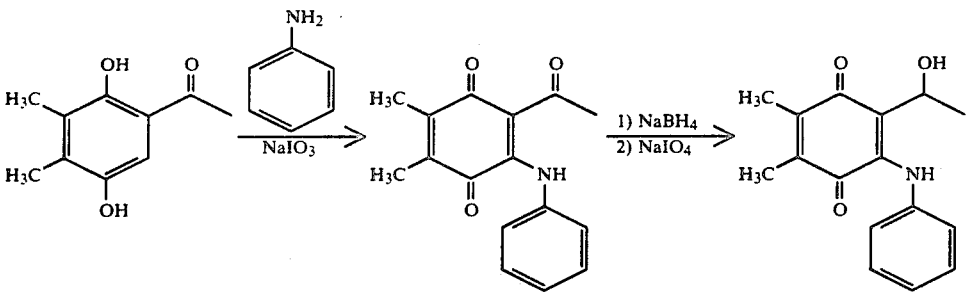

$^b$IR spectrum of this sample was measured as pure liquid.

magnesium sulfate. The solution was concentrated to afford dark purple oil (2). To the mixture was added benzene (32 mL), benzladehyde (1.1 mL, 10.8 mmol) and a catalytic amount of camphorsulfonic acid. The mixture was stirred for 2 hours at reflux under nitrogen atmosphere. The mixture was washed with sodium bicarbonate solution then brine. The solution was dried and concentrated to give dark russet color amorphous solid. This was recrystallized from ethanol to give pale purple solid (3) (1.7 g, 76% yield). Mp 148.5°–149.0° C.

$^1$H NMR (270 MHz, CDCl$_3$) delta 7.52–7.57 (m, 2H), 7.35–7.42 (m, 3H), 7.20–7.28 (m, 2H), 7.07 (br d, 2H, J=7.6 Hz), 6.97 (br t, 1H, J=7.6 Hz), 6.71 (s, 2H), 6.55 (s, 1H), 4.33 (s, 1H, OH), 2.11 (s, 3H), 2.10 (s, 3H). IR (KBr) v 1600, 1513.

To a stirred solution of the acetal (3) (1 g, 3 mmol) in acetic acid (4 ml) was added sodium cyanoborohydride (300 mg, 4.7 mmol) at room temperature. The mixture was stirred for 20 minutes and then extracted with ether. The extract was washed with brine and dried over magnesium sulfate. The solution was concentrated in vacuo to afford a pale russet color oil (4) (1 g). This hydroquinone was dissolved in methanol (10 ml), and then sodium iodate (1 g, 5 mmol) in water (10 ml) was added. The mixture was stirred for 2 hours. To this mixture was added sodium periodate (600 mg, 2.8 mmol) in order to complete the oxidation. The mixture was stirred for 1 minute, and then the mixture was diluted with water (50 ml) and ethyl acetate (100 ml). The separated organic layer was washed with brine and dried over magnesium sulfate. The solution was concentrated in vacuo to give a russet color oil (approx. 500 mg). Silica gel column chromatography eluted with hexane/ethyl acetate (20/1 - 15/1) followed by crystal- To a stirred suspension of the 2-acetyl-5,6-dimethylhydroquinone (1.8 g, 10 mmol) in methanol-water (1:2, 396 mL) was added aniline (2.48 g, 26.6 mmol) in methanol (33 mL). The mixture mostly became yellow clear solution. To the mixture was added sodium iodate in hot water (67 mL) and was stirred for 24 hours. The resulted precipitate was collected by suction filtration and extracted with ethyl acetate and water. The filtration was concentrated until 300 mL then extracted with ethyl acetate (200 mL×2). The extract was washed with brine. The combined extracts were dried over magnesium sulfate and then concentrated. Chromatography on silica gel eluted with hexane-ethyl acetate (20:1 to 10:1) to afford the desired fraction. This was concentrated in vacuo to afford brown-russet color powder (2.8 g). This was recrystallized from ethanol to afford brown-russet color needle (2.0 g, 74.3%). Mp 115.4°–116.3° C.

$^1$H NMR (270 MHz, CDCl$_3$) delta 12.97 (br s, 1H), 7.22–7.41 (m, 3H), 7.06 (d, 2H, J=6.8 Hz), 2.63 (s, 3H), 2.10 (br s, 3H), 1.96 (br s, 3H).

IR (KBr) v 1675, 1625, 1605.

To a stirred solution of the 3-acetyl-2-anilino-5,6-dimethyl-1,4-benzoquinone (700 mg, 2.6 mmol) in tetrahydrofuran-water (5:4, 12.5 mL) was added sodium borohydride (197 mg, 5.2 mmol) at room temperature. The mixture was stirred at room temperature for 10 minutes. 1N hydrochloric acid (1 mL) and ethyl acetate (50 mL) were added and the mixture was stirred for 10 minutes. The organic layer was washed with sodium bicarbonate solution and brine. The solution was dried over magnesium sulfate and concentrated in vacuo to give pale red oil. This product was dissolved in methanol (7 mL). To the solution was added sodium periodate in water at room temperature. The mixture was stirred for 5 minutes then extracted with ethyl acetate (50 mL) and washed with brine (10 mL×4). The solution was dried over magnesium sulfate and concentrated in vacuo to give a dark red oil. This was subjected to a silica gel column eluted with ethyl acetate hexane (1:3.5). The desired red color fraction was crystallized from hexane-diisopropyl ether to give red powder of the title compound (380 mg, 54% yield). Mp 101.2°–101.6° C.

$^1$H NMR (270 MHz, CDCl$_3$) delta 7.07–7.41 (m, 6H), 4.40–4.53 (m, 1H), 3.77 (d, 1H, J=11 Hz), 2.05 (s, 3H), 2.04 (s, 3H), 1.29 (d, 3H, J=6.6 Hz).

IR v 3500, 3200, 1600.

Similarly the following compounds were prepared.

eight carbon atoms and Z is hydrogen or methoxyethoxymethyl;

$R^2$ is hydrogen or phenyl;

$R^3$ is (a) cycloalkyl having three to seven carbon atoms, (b) cycloalkylalkyl having five to seven carbon atoms (c) a moiety of the formula

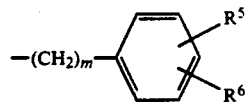

wherein m is an integer of 0 to 3 and $R^5$ and $R^6$ are each hydrogen, halo, carboxy, carbamoyl, carboalkoxy having two to four carbon atoms, alkox-

| Example No. | $R^1$ | $R^2$ | $R^3$ | m.p. | IR(KBr, cm$^{-1}$) | $^1$H NMR(270MHz, CDCl$_3$, δ) |
|---|---|---|---|---|---|---|
| 30 | CH$_2$OH | H | phenyl | 103–105° C. | 3550, 3350, 1640 1590 | 7.07–7.42(m, 6H), 4.13(d, 2H, J=7Hz) 2.73(t, 1H, J=7Hz), 2.08(br s, 3H) 2.06(br s, 3H) |
| 31$^b$ | OMEM / CH$_3$ | H | phenyl | oil | 3300, 1668, 1650 1600 | 7.70(br s, 1H), 7.28(br t, 2H, J=7.4Hz) 7.08(br t, 1H, J=7.4Hz) 6.90(br d, 2H, J=7.4Hz) 5.15(q, 1H, J=7.0Hz) 4.71(dd, 2H, J=9.2, 6.6Hz) 3.55–3.77(m, 2H), 3.48–3.54(m, 2H) 3.36(s, 3H), 2.03(s, 3H) 1.97(s, 3H), 1.40(d, 3H, J=7.0Hz) |
| 32$^b$ | OH / (CH$_2$)$_3$CO$_2$Me | H | phenyl | oil | 3320, 1730, 1650 1590 | 7.26–7.41(m, 3H), 7.12–7.26(m, 3H) 4.24(dt, 1H, J=5, 11Hz) 3.76(d, 1H, J=11Hz), 3.62(s, 3H) 2.13(t, 2H, J=7Hz), 2.04(s, 6H) 1.72–1.82(m, 1H), 1.48–1.62(m, 2H) 1.22–1.38(m, 1H) |
| 33 | OH / (CH$_2$)$_3$SO$_2$H | H | phenyl | 141–143° C. (dec) | 1700, 1660, 1580 1510 | 7.12(m, 6H), 4.23(br s, 1H) 3.82(br s, 1H), 2.16(t, 2H, J=7Hz) 2.04(s, 6H), 1.75–1.85(m, 2H) 1.48–1.63(m, 2H), 1.23–1.36(m, 2H |

$^b$IR spectrum of this sample was measured as pure liquid.

We claim:

1. A compound of the formula

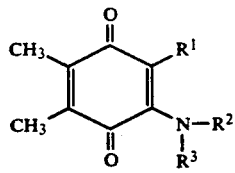

or the pharmaceutically acceptable salts thereof, wherein:

$R^1$ is hydrogen, alkyl having one to five carbon atoms, cycloalkyl having three to seven carbon atoms, phenylalkyl having from seven to nine carbon atoms, —COR$^4$ where R$^4$ is alkyl having from one to five carbon atoms, phenyl, hydroxy, amino, alkoxy having one to five carbon atoms, omega-carboxyalkyl having two to five carbon atoms, omega-alkoxycarbonylalkyl having from three to eight carbon atoms or —CH(OZ)R$^8$ where R$^8$ is hydrogen, alkyl having one to three carbon atoms, omega-carboxyalkyl having two to five carbon atoms or omega-alkoxycarbonyl having three to ycarbonylmethyl having three to five carbon atoms, or sulfamoyl or (d) substituted alkyl of the formula R$^7$-alkyl wherein said alkyl contains from five to twelve carbon atoms and R$^7$ is hydroxy, carboxy, carboalkoxy having two to four carbon atoms, hydroxyalkoxy having two to four carbon atoms or furyl; and R$^2$ and R$^3$ when taken together with the nitrogen atom to which they are attached form a structure of the formula

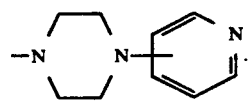

2. A compound of claim 1, wherein $R^1$ and $R^2$ are each hydrogen.

3. The compound of claim 2, wherein $R^3$ is a moiety of the formula

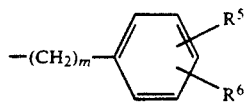

where m is 0, and $R^5$ and $R^6$ are each hydrogen.

4. The compound of claim 2, wherein $R^3$ is 2-furfuryl.

5. A compound of claim 1, wherein $R^1$ is —$COR^4$ or —$CH(OZ)R^8$ wherein $R^4$ is alkyl having one to five carbon atoms, $R^8$ is hydrogen or alkyl having one to three carbon atoms, Z is hydrogen and $R^2$ is hydrogen.

6. The compound of claim 5, wherein $R^1$ is —$COR^4$ where $R^4$ is methyl and $R^3$ is a moiety of the formula

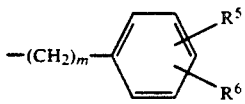

where m is 0 and $R^5$ and $R^6$ are each hydrogen.

7. The compound of claim 5, wherein $R^1$ is —CH(OZ)$R^8$ where $R^8$ is methyl and $R^3$ is a moiety of the formula

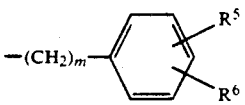

where m is 0 and $R^5$ and $R^6$ are each hydrogen.

8. The compound of claim 5, wherein $R^1$ is —CH(OZ)$R^8$ wherein $R^8$ is hydrogen and $R^3$ is a moiety of the formula

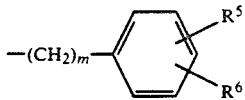

wherein m is 0 and $R^5$ and $R^6$ are each hydrogen.

9. A compound of claim 1, wherein $R^2$ and $R^3$ when taken together with the nitrogen atom to which they are attached form a structure of the formula

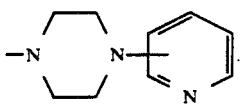

10. The compound of claim 9, wherein $R^1$ is hydrogen and $R^2$ and $R^3$ when taken together with the nitrogen atom to which they are attached form a structure of the formula

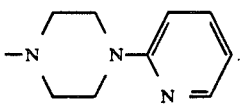

11. A method for treating an allergic or inflammatory condition in a human being in need of such treatment which comprises administering to said human being an antiallergic or antiinflammatory effective amount of a compound according to claim 1.

12. A pharmaceutical composition useful as an antiallergic or antiinflammatory agent for administration to a human subject which comprises an antiallergic or antiinflammatory amount of a compound according to claim 1 and a pharmaceutically acceptable carrier or diluent.

* * * * *

UNITED STATES PATENT AND TRADEMARK OFFICE
CERTIFICATE OF CORRECTION

PATENT NO. : 5,104,874
DATED : April 14, 1992
INVENTOR(S) : Takafumi Ikeda, et al.

It is certified that error appears in the above-identified patent and that said Letters Patent is hereby corrected as shown below:

At column 21, in the table, under heading $R^1$, at Example 33, delete " 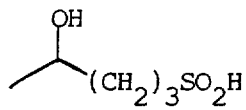 " and insert therefor -- 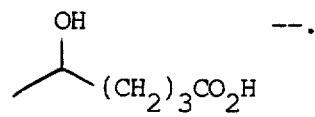 --.

Signed and Sealed this

Sixth Day of July, 1993

*Attest:*

MICHAEL K. KIRK

*Attesting Officer*  *Acting Commissioner of Patents and Trademarks*